United States Patent [19]

Burzynski

[11] Patent Number: 4,918,193

[45] Date of Patent: Apr. 17, 1990

[54] METHODS FOR PREPARING 3-[N-PHENYL-ACETYLAMINOPIPERIDINE]-2,6-DION

[76] Inventor: Stanislaw R. Burzynski, #5 Concord Cir., Houston, Tex. 77024

[21] Appl. No.: 295,372

[22] Filed: Jan. 11, 1989

[51] Int. Cl.$^4$ ............................................. C07D 211/40
[52] U.S. Cl. ..................................... 546/220; 514/328
[58] Field of Search ......................... 546/220; 514/328

[56] References Cited

U.S. PATENT DOCUMENTS 4,558,057 12/1985 Burzynski ........................... 546/220

OTHER PUBLICATIONS

Burzynski, "Synthetic Antineoplastons and Analogs", Drugs of the Future, 11:679–688, (1986).

Burzynski, "Antineoplaston A10", Drugs of the Future, 10:103–105, (1985).

Primary Examiner—Glennon H. Hollrah
Assistant Examiner—Ba K. Trinh
Attorney, Agent, or Firm—Arnold, White & Durkee

[57] ABSTRACT

Disclosed is a process for synthesizing 3-[N-phenylacetylaminopiperidine]-2,6-dion, which process comprises the steps of providing a quantity of L-glutamine, providing a quantity of phenylacetyl halide, mixing together the L-glutamine and phenylacetyl halide in a weakly alkaline aqueous solution to provide an aqueous reaction mixture, adjusting the reaction mixture to a pH ranging from about 2 to about 3, and recovering from the reaction mixture the product 3-[N-phenylacetylamino-piperidine]-2,6-dion, and when desired preparing the pharmaceutically acceptable salts thereof.

3 Claims, No Drawings

METHODS FOR PREPARING 3-[N-PHENYL-ACETYLAMINOPIPERIDINE]-2,6-DION

BACKGROUND OF THE INVENTION

The present invention relates generally to medicinal compositions and the use thereof; and more particularly, it relates to compositions of biologically active peptides and amino acid derivatives useful in the treatment of human neoplastic disease.

The practically infinite variety of peptides that can be formed by the combination of the twenty common amino acids has prompted many investigators to suggest that peptides may constitute a system carrying information from cell to cell and organ to organ. Following this view on the regulatory significance of peptides, researchers have isolated urinary peptides and amino acid derivatives which exert an influence on blood pressure, behavior modification, cardiovascular regulation, ahnd smooth muscle activity.

Accordingly, it has been considered by a number of researchers that neoplastic growth may be controlled by naturally occurring biochemical defense mechanisms. The immunological process has most often been attributed with antineoplastic activity. (See, for example, Aoki et al, *Prog. Exp. Tumor Res.*, 19: 23 (1974)). There are, however, other possible mechanisms.

It has been suggested that neoplasia is a disease of cell differentiation. Given large number of differentiating cells and assuming the possibility of error in the program for differentiation, groups of abnormally growing cells can often arise under the influence of carcinogenic factors. Without a reliable mechanism for "normalizing" such erroneously developed cells, the organisms would not live very long. Such a mechanism should be able to correct the growth of newly developed neoplastic cells and direct them into normal differentiation pathways. It is Applicant's belief that peptides are ideal compounds to function as information-carrying molecules regulating cell differentiation.

In recent years, Applicant has described a number of medium-sized peptides and amino acid derivatives which demonstrated inhibition of DNA synthesis and mitosis in cultures of various neoplastic cells without significant inhibition of normal cell replication. (See Burzynski, *Physiol. Chem. Phys.*, 5: 437 (1973); Burzynski et al, *Fed. Proc.*, 32: 766 (1973); Burzynski et al, *Physiol. Chem. Phys.* 8: 13 (1976); Burzynski et al, *Fed. Proc.*, 35: 623 (1976); Gross et al, *Physiol. Chem. Phys.*, 8: 275 (1976); Burzynski et al, *Physiol. Chem. Phys.*, 9: 485 (1977); Burzynski, U.S. Pat. Nos. 4,470,970 and 4,558,057.)

SUMMARY OF THE INVENTION

The invention in one aspect pertains to the process of synthesizing the compound 3-[N-phenylacetylaminopiperidine]-2,6-dion, which process comprises the steps of providing a quantity of L-glutamine, providing a quantity of phenylacetyl halide, mixing together the L-glutamine and phenylacetyl halide in a weakly alkaline aqueous solution to provide an aqueous reaction mixture, thereafter bringing the reaction mixture to a pH ranging from about 2 to about 3, incubating the reaction mixture for a period of time to form the reaction product 3-[N-phenylacetylaminopiperidine]-2,6-dion, and recovering from the reaction mixture the product 3-[N-phenylacetyl-yl-aminopiperidine]-2,6-dion, and when desired preparing the pharmaceutically acceptable salts thereof.

The present invention provides for a greater yield of the reaction product 3-[N-phenylacetylaminopiperidine]-2,6-dion than would normally occur by simple reaction of L-glutamine and phenylacetyl halide ina weakly alkaline solution. By lowering the pH of the reaction mixture to a pH ranging from about 2 to 4, the subsequent hydrolysis of 3-[N-phenylacetylaminopiperidine]-2,6-dion to its degradation products is stalled. Further, lowering the pH facilitates the separation of the reaction mixture into two layers thereby rendering more easily the isolation of the desired product.

DESCRIPTION OF THE PREFERRED EMBODIMENTS

The invention will be described in terms of preferred embodiments known to the Applicant at the time of this application which represent the best mode corresponding to the synthesis, and purification of 3-[N-phenylacetylaminopiperidine]-2,6-dion.

The structure of 3-[N-phenylacetylaminopiperidine]-2,6-dion is depicted below.

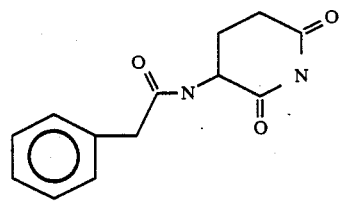

Its chemical structure was confirmed by mass spectrometry, $13_C$(NMR) spectroscopy, and infrared spectrometry.

Synthesis of 3-[N-phenyl-acetylaminopiperidine]-2,6-dion

Sodium bicarbonate (16 moles) and L-glutamine (4 moles) were dissolved in deionized water (20 liters) then stirred for 7 minutes at 20°–25° C. Phenylacetyl chloride (6 moles) was gradually added over a period of 1 hour to the reaction mixture and vigorously stirred for 45 minutes. The solution was adjusted to pH 2.5 with concentrated hydrochloric acid. Thereafter, the reaction mixture was evaporated at 75° C. under vacuum until the material began to precipitate.

The resulting material was stored at 4° C. for 24 hours. Afterward, the lower layer was collected and heated to 160° C., and the resulting residue was cooled to 75° C. Thereafter, deionized water was added to the residue and the mixture was stored at 4° C. for 12 hours. The precipitate which formed was collected and dissolved in methanol. Activated charcoal (U.S.P.) was added to the methanol solution and afterward filtered. The filtrate was collected and stored at 4° C. for 12 hours. Upon storing, a precipitate formed which was then filtered and freeze dried. The freeze dried material corresponded to 3-[N-phenylacetylaminopiperidine]-2,6-dion.

Preparation of 3-[N-phenylacetylaminopiperidine]-2,6-dion for Injection

Five thousand grams of 3-[N-phenylacetylaminopiperidine]-2,6-dion was pulverized in a grinder, then suspended in 44 liters of pyrogen-free water. Concentrated sodium hydroxide in pyrogen-free water was added stepwise and stirred until all the powder was dissolved. The pH of the mixture was 7.0. Activated charcoal (U.S.P.) was added and stirred for 45 minutes, and then filtered. The concentration of the filtrate was adjusted to 103 mg/ml with pyrogen free water. The filtrate was then processed according to standard U.S.P. procedure for large volume injections of single dose infusions.

Upon standing, 3-[N-phenylacetylaminopiperidine]2,6-dion sodium salt undergoes basic hydrolysis to form the sodium salts of phenylacetyl glutamine and phenylacetyl isoglutamine, generally in a 4:1 ratio.

Preparation of Phenylacetyl Glutamine

Phenylacetyl glutamine was first described by Thierfelder and Sherwin (see *J. Physiol. Chem.* 94: 1 (1915)) as a constituent of normal human urine. In later investigations of the compound, phenylacetyl glutamine was shown to have a slight effect on the growth of murine tumors (see Lichtenstein et al, Israel, Israel *J. Med. Sci.*, 13: 316 (1977)) but there was no indication that the compound was useful in the treatment of human cancer. The sodium salt of phenylacetic acid was used by Neish in the treatment of Rd/3 sarcoma in rats but failed to inhibit tumor growth. Indeed, the results suggested that the treatment with phenylacetic acid caused some enhancement of tumor growth (see Neish, *Experientia*, 27: 860 (1971)). Applicant has demonstrated in his clinical studies that phenylacetyl glutamine alone and a mixture of phenylacetyl glutamine and phenylacetic acid are each useful in the treatment of human cancers.

L-glutamine (4 moles) and sodium bicarbonate (16 moles) were added to 20 liters of deionized water, and stirred at a temperature of 20°-25° C. for 7 minutes. Phenylacetyl chloride (6 moles) was added over a period of one hour and stirred for 45 minutes. The pH of reaction was brought to 2.5 with concentrated hydrochloric acid. The reaction mixture was extracted with methylene chloride three times. The water layer was decanted, and adjusted pH to 7.0 by concentrated sodium hydroxide, and evaporated until material started to precipitate. The pH of the solution was adjusted to 2.3, and extracted with ethyl acetate. Thereafter, the solution was filtered and freeze dried.

Antineoplastic Compositions

A mixture of the sodium salts of phenylacetyl glutamine and phenylacetic acid in the ratio of 1 to 4 is the preferred injectable formulation for use in the treatment of human cancer.

For oral administration, capsule formulations of 3-[N-phenylacetylaminopiperidine]-2,6-dion (500 mg), together with 500 mg of a 1 to 4 ratio of the sodium salts of phenylacetyl glutamine and phenylacetic acid, are preferred.

Solutions for parenteral administrations are prepared by reconstituting the respective chemicals in form of sodium salts in pyrogen free water to the desired total concentrations, for example 100 mg/ml. The pH of the solution is adjusted to 7.0 with 1N NaOH or 1N HCl. Sterilization of the reconstituted solution is done by filtration according to the guidelines of the U.S. Pharmacopeia. The sterility of the material is tested as required by the rules and regulations of the Food and Drug Administration, Section 610.12. The resulting sterile formulations are suitable for parenteral injections.

If the reconstituted lyophilized 3-[N-phenylacetylaminopiperidine]-2,6-dion or its degradation products phenylacetyl glutamine and phenylacetyl isoglutamine are not to be used immediately, the prevention of microbial proliferation can be attained by the addition of various antibacterial and antifungal agents to the solutions, for example, parabens, chlorobutanol, benzyl alcohol, phenol, sorbic acid, thimerosol, and the like. In many instances, it will be desirable to include isotonic agents to the injectable solutions, for example, sugars or sodium chloride.

Antineoplastic Activity of 3-[N-phenylacetylaminopiperidine]-2,6-dion

The antineoplastic activity of 3-[N-phenylacetylaminopiperidine]-2,6-dion and its degradation products was first evaluated experimentally by observing the cytostatic effects of the preparations would have on a tumor line as compared to the overall toxicity the preparation would have on experimental animals. Accordingly, the preparation having the greatest cytostatic activity and the lowest animal toxicity are said to have the better antineoplastic activity, or therapeutic effectiveness.

The cytostatic activity of 3-[N-phenylacetylaminopiperidine]-2,6-dion was tested in a culture of human carcinoma of the breast line MDA-MB-231 obtained from M. D. Anderson Cancer Institute, Houston, Tex. MDA-MB-231 is a fast growing line of human breast cancer established by Cailleau et al, *J. Natl. Cancer Inst.*, 53: 661 (1974). The estimated doubling time of these cells is 18 hours when grown in the original medium described by Beall et al, *Physiol. Chem. Physics*, 8: 281 (1976). Briefly, to summarize the preferred medium and method, the cells were grown in monolayers at 37° C. in Leilbovitz L-15 medium supplemented with 20% fetal bovine serum, 1.6 µg/ml glutathione, 0.25 U/ml insulin, 100 ug/ml disodium carbenicillin and 100 µg/ml gentamycin.

For the bioassay, 3-[N-phenylacetylaminopiperidine]-2,6-dion was dissolved in the above-described medium at four different concentrations selected arbitrarily within the range of 0.5 to 50 mg/ml. Monolayer cultures were incubated with the 3-[N-phenylacetylaminopiperidine]-2,6-dion containing medium for 96 hours. The cells were counted visually at 24 hour intervals. Control cultures were grown in the standard medium without added 3-[N-phenylacetylaminopiperidine]-2,6-dion.

3-[N-phenylacetylaminopiperidine]-2,6-dion in concentrations of 2 mg/ml produces a cytostatic effect in such human breast carcinoma cultures. The cytostatic effect is determined as a stable number of cells (within the limits from 80% to 120%) counted after 24 hours from incubation and persisting for at least an additional 48 hours.

The cytostatic concentration of the degradation products phenylacetyl glutamine and phenylacetic acid were determined in the same manner described above.

The cytostatic concentration for each antineoplastic compound is as follows:

| Antineoplastic Compound | Cytostatic Concentration |
| --- | --- |
| 3-[N-phenylacetylamino-piperidine]-2,6-dion | 2 mg/ml |
| Phenylacetyl glutamine | 10 mg/ml |
| Phenylacetyl glutamine and Phenylacetic acid (1:4 mixture) | 3 mg/ml |

Above these concentrations, all antineoplastic compounds produce cytotoxic effect in human breast carcinoma cultures.

Acute toxicity studies on experimental animals reveal that 3-[N-phenylacetylaminopiperidine]-2,6-dion has very low toxicity. For example, experiments involving HA/ICR swiss mice injected intraperitoneally with 3-[N-phenylacetylaminopiperidine]-2,6-dion resulted in a $LD_{50}$ of 10.33 g/kg. The autopsy and microscopic studies of the tissues of the animals which died during the experiment revealed congestion of the liver and marked pulmonary edema. The animals which survived were kept for one week under close observation and were noted to carry on normal activity. After a week, a select number of the mice were sacrificed. The autopsy and microscopic examination of the tissues of these animals were identical to those of control, uninjected subjects.

Acute toxicity studies involving phenylacetyl glutamine and phenylacetic acid were carried out in the same manner described above. The respective $LD_{50}$ for mice for each fraction is as follows:

| Antineoplastic Compound | $LD_{50}$ |
| --- | --- |
| 3-[N-phenylacetylamino-piperidine]-2,6-dion | 10.33 g/kg |
| Phenyl acetyl glutamine | 2.90 g/kg |
| Phenyl acetyl glutamine and Phenyl acetic acid (1:4) Mixture | 2.83 g/kg |

Clinical Evaluation of
3-[N-phenylacetylaminopiperidine]-2,6-dion

The definitions of remission associated with neoplastic disease are as follows: complete remission is the disappearance of all clinical evidence of disease and partial remission is reduction by at least 50% in the sum of the products of two perpendicular diameters of all measurable disease lasting at least four weeks. Patients are considered stabilized if measurable tumor regression occurs but does not meet the criteria for partial remission.

Various human neoplastic diseases were treated with 3-[N-phenylacetylaminopiperidine]-2,6-dion or its degradation products. For each neoplastic disease studied, 3-[N-phenylacetylaminopiperidine]-2,6-dion and its degradation products, phenylacetyl glutamine and phenylacetyl isoglutamine, and a combination of phenylacetyl glutamine and phenylacetic acid, were effective to some extent in aiding the regression of tumors. As would be expected, some compositions exhibited more effectiveness for some forms of neoplasia than other compositions.

The dosage of the selected antineoplastic agent for the treatment of the indicated neoplastic condition depends on the age, weight and condition of the patient; the particular neoplastic disease and its severity; and the route of administration.

EXAMPLE 1

The phase I clinical studies with 3-[N-phenylacetylaminopiperidine]-2,6-dion 500 mg capsules involved 42 patients diagnosed with 49 types of advanced neoplastic diseases. The formulation was administered daily for from 6 to 314 days. The highest dosage taken was 288.4 mg/kg/24 hours. The treatment was associated with minimal adverse reactions, including excessive gas, gastrointestinal bleeding (most likely not related to 3-[N-phenylacetylaminopiperidine]-2,6-dion but to primary disease), moderately increased blood pressure, skin rash, vertigo, hypokalemia, hypoglycemia and mild myelosuppression. Positive clinical response was obtained in 75% of 49 treated cases. Desirable side effects of the treatment included decrease of plasma levels of triglycerides and cholesterol, increase of white blood cell count, red blood cell count and platelet count, and improvement of blood clotting. The best clinical effects were observed in chronic myelocytic leukemia and chronic lymphocytic leukemia, adenocarcinoma of the prostate, carcinoma of the breast and glioma.

EXAMPLE 2

Phase I clinical trials with a 4:1 mixture of sodium salts of phenylacetyl glutamine and phenylacetyl isoglutamine injections involved 18 patients diagnosed with 19 types of neoplastic diseases. The patients' diagnoses included adenocarcinoma of the rectum and colon stage IV (8 cases), adenocarcinoma of the pancreas (4 cases), adenocarcinoma of the breast stage IV (3 cases), and single cases of the adenocarcinoma of the lung stage III, adenocarcinoma of the stomach stage IV, chondrosarcoma and carcinoid. The formulation was administered daily in divided doses intravenously via subclavian vein catheter for from 52 to 640 days. The highest dosage taken was 2210.5 mg/kg/24 hours. However, most patients received from 206.9 to 397.1 mg/kg/24 hours. Only minimal adverse effects were noticed sometime during the course of the treatment. They included febrile reactions, muscle and joint pain, muscle contractions in the throat, abdominal pain of short duration and single incidences of nausea, dizziness and headache. Desirable side effects included increase of platelet count and white blood cell count. Eight patients had objective responses to the treatment

EXAMPLE 3

Phase I clinical studies of phenylacetyl glutamine injections involved 13 patients diagnosed with 15 types of neoplastic diseases. The formulations was administered intravenously via subclavin vein catheter for from 41 to 436 days. The highest dosage was 168 mg/kg/24 hours. The treatment was free from significant side effects, with the exception of febrile reactions and swelling of the small joints observed sporadically during the treatment. Desirable side effects included increase of platelet count and increase of concentration of plasma globulin. Objective responses included 2 complete remissions and 1 mixed response. In addition, 4 cases were classified as stable, which 6 cases were progressive. Complete remission was obtained in squamos cell carcinoma of the larynx stage II and large cell undifferentiated carcinoma of the lung with lymph node and liver metastases. Mixed response was observed in 1 case of carcinoma of the breast with metastases to the lymph nodes, skin and liver (complete remission of liver metastases but increasing skin metastases). The patient diagnosed with lung cancer and lymph node and liver metastases continues to be in complete remission 5 years after the study was done.

EXAMPLE 4

Phase I clinical trials with 1:4 mixture of phenylacetyl glutamine and phenylacetic acid injections involved 20 patients diagnosed with 21 types of neoplastic diseases. The patients' diagnose included lung cancer stage III (4 cases), colorectal stage IV (3 cases), breast stage IV (2 cases), breast in remission (1 case), glioblastoma (3 cases), head and neck storage IV (3 cases), uterine cervix stage I-A (1 case), chronic myelocytic leukemia (2 cases), lymphocytic lymphoma stage IV (1 case) and leiomyosarcoma of the uterus stage IV-B (1 case). Antineoplaston AS2-1 was administered every 6 hours intravenously through a subclavian vein catheter for from 36 to 872 days. Most of the patients were treated for 61 to 229 days. The highest dosage taken was 160 mg/kg/24 hours. Only minimal adverse effects were noted sometime during the treatment and included slight decrease of white blood cell count, mild hypocalcemia, hypokalemia and hypertension. Responses to the therapy included 6 cases of complete remission, 2 cases of partial remission and 7 cases of stabilization, while 6 cases showed progressive disease. Five years after the study was done, 3 patients are alive and free of cancer, 9 patients have died, and the condition of the remaining 8 patients is unknown.

Implementation of 3-[N-phenylacetylaminopiperidine]-2,6-dion, phenylacetyl glutamine and a combination of phenylacetyl glutamine and phenylacetic acid has been directed with success in the regression of tumors associated with human cancer of the esophagus, breast cancer, bladder cancer, colon cancer, large cell undifferentiated carcinoma of the lung, adenocarcinoma and squamous cell carcinoma of the lung, brain metastases, bone metastases, lung metastases, prostate cancer, pancreas cancer, lymphatic lymphoma, uterine cervix cancer, primary malignant brain tumor.

The foregoing description of the invention has been directed to a particular example of synthesizing 3-[N-phenylacetylaminopiperidine]-2,6-dion for purposes of explanation and illustration. It should be understood, however, that many modifications and changes in the synthesis of 3-[N-phenylacetylaminopiperidine]-2,6-dion can be made in the implementation and utilization of the present invention without departing from the scope of the invention defined in the claims.

What is claimed is:

1. A process for synthesizing the compound 3-[N-phenylacetylaminopiperidine]-2,6-dion, consisting essentially of the steps in sequence of:
   providing a quantity of L-glutamine;
   providing a quantity of phenylacetyl halide;
   mixing together the L-glutamine and phenylacetyl halide in a weakly alkaline aqueous solution;
   adjusting the weakly alkaline aqueous solution to a pH ranging from about 2 to about 3, to form an acidic reaction mixture;
   heating the acidic reaction mixture to about 160° C. and thereafter allowing it to cool;
   recovering from the acidic reaction mixture the product 3-[N-phenylacetylaminopiperidine]-2,6-dion, and when desired preparing the pharmaceutically acceptable salts thereof.

2. The process according to claim 1 wherein the phenylacetyl halide is phenylacetyl chloride.

3. The process according to claim 1 wherein the pH is adjusted with concentrated HCl.

* * * * *